(12) United States Patent
Ghose et al.

(10) Patent No.: US 10,957,010 B2
(45) Date of Patent: Mar. 23, 2021

(54) DEFORMABLE REGISTRATION FOR MULTIMODAL IMAGES

(71) Applicant: General Electric Company, Schenectady, NY (US)

(72) Inventors: Soumya Ghose, Niskayuna, NY (US); Jhimli Mitra, Niskayuna, NY (US); David Martin Mills, Niskayuna, NY (US); Lowell Scott Smith, Niskayuna, NY (US); Desmond Teck Beng Yeo, Clifton Park, NY (US); Thomas Kwok-Fah Foo, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 110 days.

(21) Appl. No.: 16/534,785

(22) Filed: Aug. 7, 2019

(65) Prior Publication Data
US 2021/0042878 A1 Feb. 11, 2021

(51) Int. Cl.
*G06T 3/00* (2006.01)
*G06T 11/00* (2006.01)
*A61B 8/08* (2006.01)
*G01R 33/56* (2006.01)

(52) U.S. Cl.
CPC .......... *G06T 3/0068* (2013.01); *A61B 8/5207* (2013.01); *G01R 33/56* (2013.01); *G06T 11/006* (2013.01); *G06T 2210/41* (2013.01)

(58) Field of Classification Search
CPC .................................................. G06T 3/0068
See application file for complete search history.

(56) References Cited

U.S. PATENT DOCUMENTS

| 2012/0215093 | A1* | 8/2012 | Ji | A61B 6/5247 600/411 |
| 2016/0217560 | A1* | 7/2016 | Tahmasebi Maraghoosh | A61B 5/0033 |
| 2017/0103540 | A1* | 4/2017 | Brokman | A61B 6/5247 |
| 2017/0231771 | A1* | 8/2017 | Piron | A61B 5/1079 606/102 |

\* cited by examiner

*Primary Examiner* — Oneal R Mistry (57) ABSTRACT

The subject matter discussed herein relates to the automatic, real-time registration of pre-operative magnetic resonance imaging (MRI) data to intra-operative ultrasound (US) data (e.g., reconstructed images or unreconstructed data), such as to facilitate surgical guidance or other interventional procedures. In one such example, brain structures (or other suitable anatomic features or structures) are automatically segmented in pre-operative and intra-operative ultrasound data. Thereafter, anatomic structure (e.g., brain structure) guided registration is applied between pre-operative and intra-operative ultrasound data to account for non-linear deformation of the imaged anatomic structure. MR images that are pre-registered to pre-operative ultrasound images are then given the same nonlinear spatial transformation to align the MR images with intra-operative ultrasound images to provide surgical guidance.

20 Claims, 8 Drawing Sheets

FIG. 7

# DEFORMABLE REGISTRATION FOR MULTIMODAL IMAGES

BACKGROUND

The subject matter disclosed herein relates to automatic multimodal image registration that utilizes structure segmentation to facilitate guidance and which may be used for real-time tracking of moving objects.

Non-invasive imaging technologies allow images of the internal structures or features of a patient/object to be obtained without performing an invasive procedure on the patient/object. In particular, such non-invasive imaging technologies rely on various physical principles (such as the differential transmission of X-rays through a target volume, the reflection of acoustic waves within the volume, the paramagnetic properties of different tissues and materials within the volume, the breakdown of targeted radionuclides within the body, and so forth) to acquire data and to construct images or otherwise represent the observed internal features of the patient/object.

By way of example, magnetic resonance imaging (MRI) is a useful imaging modality in the context of surgical and interventional procedures since it provides soft tissue contrast that enables mapping of the location and boundary of pathological tissue (e.g., tumors) in the planning/diagnosis phases. However, due to the limited patient space in the magnet bore, requirement of MRI compatible surgical instruments and low imaging frame rate, it is difficult to integrate real-time MRI into surgical operation workflows. Thus, real-time MR images are typically not available in the surgical operation phase, which increases the risks of invasive access or treatment of healthy tissue regions that were not targeted in the planning phase. In addition, clinicians may fail to completely access or treat the pathological tissue due to the lack of real-time tracing of pathological tissue boundaries. While segmentation or manual tracing of a lesion/tumor from MR images in the planning phase may provide an initial location of one or more fiducials, due to physiological motion, position or orientation changes, deformation, and so forth, this initial location may not correspond to the true position and/or boundaries of the target lesion/tumor in a subsequent invasive procedure.

Ultrasound imaging, conversely, may be useful to provide real-time imaging, including during a surgical or interventional procedure. However, ultrasound imaging provides poorer soft tissue contrast, which may lead to inaccurate localization of the tissue of interest (e.g., pathological tissue, such as tumors) and/or the boundaries of such tissue. These limitations may in turn limit the ability to locate or delineate pathology or target lesions.

In certain contexts, such imaging technologies may be used together to provide or facilitate real-time tracking of moving (i.e., dynamic) objects (e.g., moving tissues or organs), such as by using a combination of imaging technologies to allow the internal structures or features of a patient/object to be recognized and monitored. In particular, such imaging targets may exist in areas of the body that move or change size and/or shape over time. The accurate tracking of such dynamic structures provides useful information in medical practice. For example, in neurosurgery it is useful for the doctor to see precisely where the brain tumor margin is in order to do proper resection without causing damage to the surrounding brain tissues. The pre-operative imaging (such as ultrasound and magnetic resonance imaging) may provide useful references for identifying a tumor boundary (e.g., a brain tumor boundary) in such a context. However, in this example, during the subsequent brain surgical operation, there are deformations of the tissues inside the skull due to the fluid and pressure loss associated with the dura opening, or due to the tumor resection. Consequently, the intra-operative images of the tumor boundary may change significantly in comparison to the pre-operative image references.

However, in such combined or multi-modal imaging context, linking real-time ultrasound imaging with pre-acquired MR images (acquired at a different time) may be time-consuming, computationally intensive, and may have inaccuracies that adversely affects the precision and outcome of the surgical operation. In addition, image contrast and spatial resolution in MRI and ultrasound imaging are different and these differences exacerbate the difficulty in aligning or registering MR and ultrasound images. Thus, there is a need for an imaging approach that provides sufficient soft tissue contrast during the intervention/treatment phase while also providing real-time positional information of the target lesion.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a method for image registration is provided. In accordance with this method, one or more pre-operative magnetic resonance (MR) images and one or more pre-operative ultrasound images are acquired. A registration is performed between the pre-operative MR images and the pre-operative ultrasound images. One or more intra-operative ultrasound images are acquired during a surgical operation. A structure-guided registration is performed between the pre-operative ultrasound images and the intra-operative ultrasound images to derive a spatial transformation that accounts for non-linear deformations. The spatial transformation is applied to the pre-operative MR images that were registered to the pre-operative ultrasound images to generate one or more transformed MR images that align with the intra-operative ultrasound images. Guidance is provided based on the transformed MR images during the surgical operation to facilitate the surgical operation.

In a further embodiment, an image registration system is provided. In accordance with this embodiment, the image registration system comprises memory encoding processor-executable routines and a processing component configured to access the memory and execute the processor-executable routines. The routines, when executed by the processing component, cause the processing component to perform actions comprising: accessing or acquiring one or more pre-operative magnetic resonance (MR) images and one or more pre-operative ultrasound images; registering the pre-operative MR images and the pre-operative ultrasound images; receiving one or more intra-operative ultrasound images generated during a surgical operation; performing a structure-guided registration between the pre-operative ultrasound images and the intra-operative ultrasound images to derive a spatial transformation that accounts for non-linear deformations; applying the spatial transformation to the pre-operative MR images that were registered to pre-operative ultrasound images to generate one or more transformed MR image that align with the intra-operative ultrasound images; and providing guidance based on the transformed MR images during the surgical operation to facilitate the surgical operation.

In an additional embodiment, a method for evaluating a surgical operation is provided. In accordance with this method one or more pre-operative magnetic resonance (MR) images and one or more pre-operative ultrasound images are acquired simultaneously or temporally consecutively. A registration is performed between the pre-operative MR images and the pre-operative ultrasound images. One or more post-surgery ultrasound images are acquired. A structure-guided registration is performed between the post-surgery ultrasound images and one of either the pre-operative ultrasound images or an intermediate transform of the pre-operative ultrasound images to derive a spatial transformation that accounts for non-linear deformations. The spatial transformation is applied to the pre-operative MR images or an intermediate transform of the MR images to generate one or more post-operation transformed MR images. Guidance is provided based on the post-operation transformed MR image regarding whether the surgical operation has been completed.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The subject matter discussed herein relates to the automatic, registration of pre-operative magnetic resonance imaging (MRI) data to intra-operative ultrasound (US) data (e.g., reconstructed images or unreconstructed data), such as to facilitate surgical guidance or other interventional procedures. In one such example, brain structures (or other suitable anatomic features or structures) are automatically segmented in pre-operative and intra-operative ultrasound data. Thereafter, anatomic structure (e.g., brain structure) guided registration is applied between pre-operative and intra-operative ultrasound data to account for non-linear deformation of the imaged anatomic structure, such as deformation of the brain due to dura opening and structural changes due to resection. MR images that are pre-registered to pre-operative ultrasound images are then given the same nonlinear spatial transformation to align the MR images with intra-operative ultrasound images to provide surgical guidance. The technique is suitable for use with, but not limited to, multimodality imaging platforms that can acquire pre-operative ultrasound and MR images simultaneously followed by intra-operative ultrasound using the same MR compatible probe or a comparable ultrasound probe. In one embodiment, an MR-compatible three-dimensional (3D) ultrasound probe suitable for simultaneous acquisition of pre-operative MRI and ultrasound images is useful for providing a suitable degree of pre-operative MRI and pre-operative ultrasound registration accuracy. In such an example, a better initialization of a deformable registration between pre-operative MRI and intra-operative ultrasound may be provided, resulting in faster and more precise registration.

With the preceding in mind, material related to imaging techniques and terms is provided below so as to impart some familiarity with such imaging systems and to provide useful real-world context for other aspects of the disclosure. With respect to magnetic resonance imaging (MRI) systems, and turning to FIG. 1 where one such system is schematically illustrated for reference, interactions between a primary magnetic field, time varying magnetic gradient fields, and a radiofrequency (RF) field with material(s) having a non-zero nuclear magnetic moment within a subject of interest (e.g., a patient) are used to generate images or volumetric representations of structural and/or functional relationships within the patient. Nuclei that have a non-zero nuclear magnetic moment, such as hydrogen nuclei in water molecules, have characteristic behaviors in response to externally applied electromagnetic fields (e.g., constant or time varying electric fields, magnetic fields, or a combination thereof) that may be leveraged in this manner. For example, the precession of spins of these nuclei can be influenced by manipulation of the fields to produce RF signals that can be detected, processed, and used to reconstruct a useful image.

Figure 1:
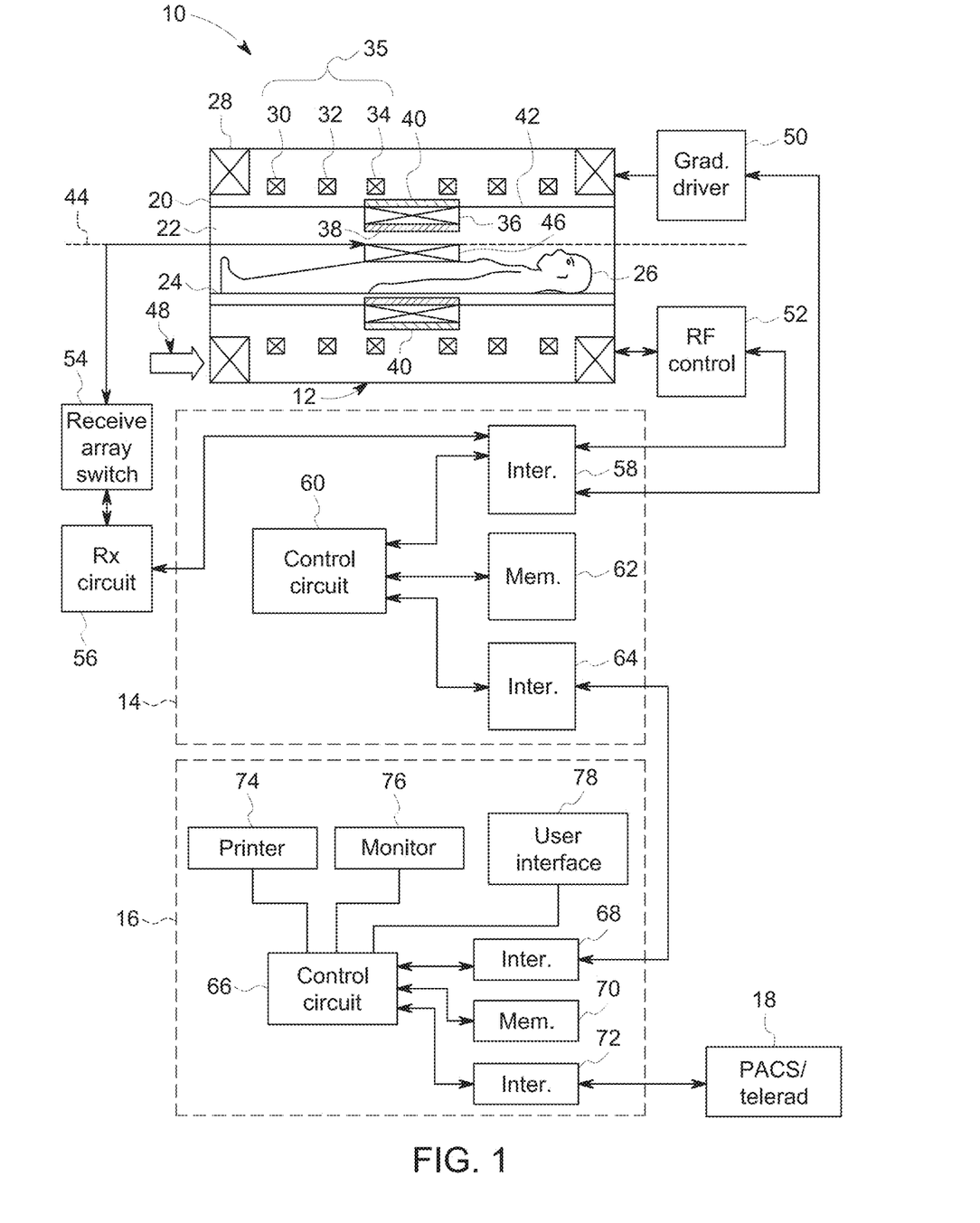
FIG. 1 illustrates a magnetic resonance imaging (MRI) system, in accordance with aspects of the present disclosure.

With this in mind, and referring to FIG. 1, a magnetic resonance imaging system 10 is illustrated schematically as including a scanner 12, scanner control circuitry 14, and system control circuitry 16. The imaging system 10 additionally includes remote access and storage systems 18 and/or devices such as picture archiving and communication systems (PACS), or other devices such as teleradiology equipment so that data acquired by the imaging system 10 may be accessed on- or off-site. While the imaging system 10 may include any suitable scanner or detector, in the illustrated embodiment, the imaging system 10 includes a full body scanner 12 having a housing 20 through which an opening (e.g., an annular opening) is formed to accommodate a patient bore 22. The patient bore 22 may be made of any suitable material such as a non-metallic and/or non-magnetic material and generally includes components of the scanner 12 proximate to a subject. A table 24 is moveable into the patient bore 22 to permit a patient 26 to be positioned therein for imaging selected anatomy within the patient 26. As described herein, the patient bore 22 may include one or more bore tubes to support various components of the scanner 12 and/or the patient 26. In some embodiments, the patient bore 22 may support the table 24 and/or articulation components (e.g., a motor, pulley, and/or slides).

The scanner 12 may include a series of associated superconducting magnet coils for producing controlled static magnetic fields for separating the allowed energy states of nuclei with non-zero magnetic moment, typically hydrogen in the body, within the anatomy of the subject being imaged. Specifically, a primary magnet coil 28 is provided for generating a primary magnetic field, which is generally aligned with an axis 44 of the patient bore 22. A series of gradient coils 30, 32, and 34 (collectively 35) permit controlled magnetic gradient fields to be generated for positional encoding of certain of the nuclei within the patient 26 during examination sequences. An RF coil 36 is configured to generate radio frequency pulses for exciting the certain nuclei with non-zero magnetic moment within the patient 26. In accordance with an aspect of the present disclosure, the RF coil 36 may be implemented on a coil support tube 38 defining at least a portion of the patient bore 22. Further, an RF shield 40 may be implemented on a shield support tube 42 also defining at least a portion of the patient bore 22 to reduce electromagnetic interference within the imaging system 10, as well as devices separate from the imaging system 10. In addition to the coils that may be local to the scanner 12, the imaging system 10 may also include a set of receiving coils 46 (e.g., an array of coils) configured for placement proximal (e.g., against) to the patient 26. As an example, the receiving coils 46 can include cervical/thoracic/lumbar (CTL) coils, head coils, single-sided spine coils, and so forth. Generally, the receiving coils 46 are placed close to or on top of the patient 26 so as to receive the weak RF signals (e.g., weak relative to the transmitted pulses generated by the scanner coils) that are generated by certain of the nuclei with non-zero magnetic moment within the patient 26 as they return to their equilibrium state. In some embodiments, the RF coils 36 may both transmit and receive RF signals accomplishing the role of the receiving coils 46.

The various coils of the imaging system 10 are controlled by external circuitry to generate the desired field and pulses, and to read emissions from precessing nuclei with non-zero nuclear magnetic moment (material) in a controlled manner. In the illustrated embodiment, a main power supply 48 provides power to the primary magnetic coil 28 to generate the primary magnetic field. A driver circuit 50 may include amplification and control circuitry for supplying current to the coils as defined by digitized pulse sequences output by the scanner control circuitry 14.

An RF control circuit 52 is provided for regulating operation of the RF coil 36. The RF control circuit 52 includes a switching device for alternating between the active and inactive modes of operation, wherein the RF coil 36 transmits and does not transmit signals, respectively. The RF control circuit 52 may also include amplification circuitry to generate the RF pulses. Similarly, the receiving coils 46, or RF coils 36 if no separate receiving coils 46 are implemented, are connected to a switch 54, which is capable of switching the receiving coils 46 between receiving and non-receiving modes. Thus, the receiving coils 46 may resonate with the RF signals produced by the transverse magnetization of nuclei with non-zero nuclear magnetic moment from within the patient 26 while in the receiving mode, and avoid resonating with RF signals while in the non-receiving mode. Additionally, a receiving circuit 56 may receive the data detected by the receiving coils 46 and may include one or more multiplexing and/or amplification circuits.

It should be noted that while the scanner 12 and the control/amplification circuitry described above are illustrated as being connected by single lines, one or more cables or connectors may be used depending on implementation. For example, separate lines may be used for control, data communication, power transmission, and so on. Further, suitable hardware may be disposed along each type of line for the proper handling of the data and current/voltage. Indeed, various filters, digitizers, and processors may be disposed between the scanner 12 and the scanner control circuitry 14 and/or system control circuitry 16.

As illustrated, the scanner control circuitry 14 includes an interface circuit 58, which outputs signals for driving the gradient coils 35 and the RF coil 36 and for receiving the data representative of the magnetic resonance signals produced in examination sequences. The interface circuit 58 may be connected to a control and analysis circuit 60. The control and analysis circuit 60 executes the commands to the driver circuit 50 and RF control circuit 52 based on defined protocols selected via system control circuitry 16.

The control and analysis circuit 60 may also serve to receive the magnetic resonance signals and perform subsequent processing before transmitting the data to system control circuitry 16. Scanner control circuitry 14 may also include one or more memory circuits 62, which store configuration parameters, pulse sequence descriptions, examination results, and so forth, during operation.

A second interface circuit 64 may connect the control and analysis circuit 60 to a system control circuit 66 for exchanging data between scanner control circuitry 14 and system control circuitry 16. The system control circuitry 16 may include a third interface circuit 68, which receives data from the scanner control circuitry 14 and transmits data and commands back to the scanner control circuitry 14. As with the control and analysis circuit 60, the system control circuit 66 may include a computer processing unit (CPU) in a multi-purpose or application specific computer or workstation. System control circuit 66 may include or be connected to a second memory circuit 70 to store programming code for operation of the imaging system 10 and to store the processed image data for later reconstruction, display and transmission. The programming code may execute one or more algorithms that, when executed by a processor, are configured to perform reconstruction of acquired data or other operations involving the acquired data.

An additional input output (I/O) interface 72 may be provided for exchanging image data, configuration parameters, and so forth with external system components such as remote access and storage systems 18. Finally, the system control circuit 66 may be communicatively coupled to various peripheral devices for facilitating an operator interface and for producing hard copies of the reconstructed images. In the illustrated embodiment, these peripherals include a printer 74, a monitor 76, and a user interface 78 including, for example, devices such as a keyboard, a mouse, a touchscreen (e.g., integrated with the monitor 76), and so forth.

In operation, a user (e.g., a radiologist) may configure and/or oversee control of the imaging system 10. Additionally, the user may assist in positioning the subject (e.g., a patient 26) within the patient bore 22. In some embodiments, the patient bore 22 may surround an entire subject or just a portion thereof (e.g., a patient's head, thorax, and/or extremity) while an imaging session is performed.

Figure 2:
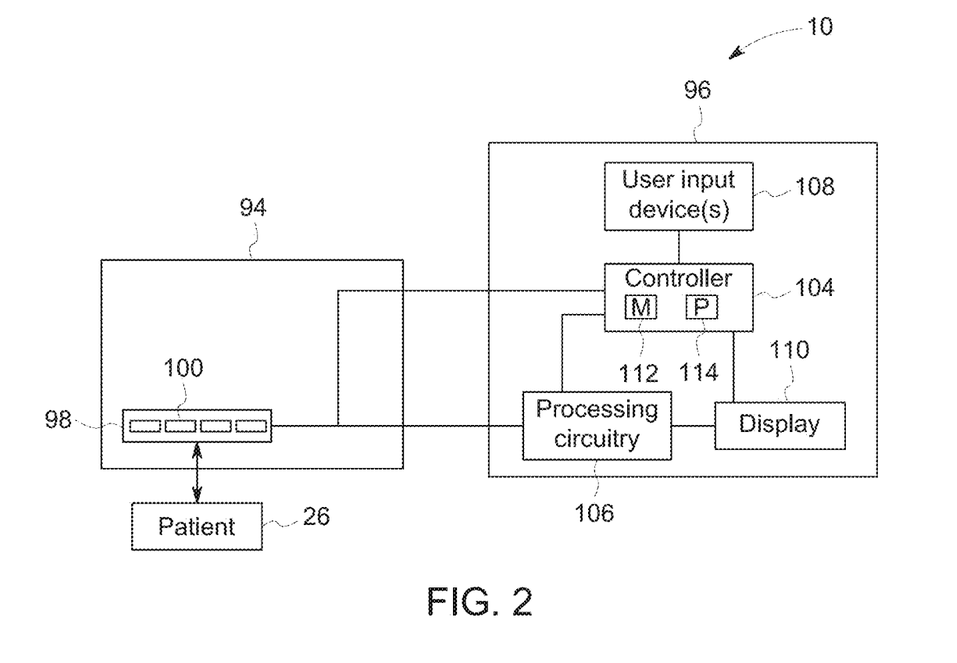
FIG. 2 is an embodiment of a block diagram of an ultrasound system, in accordance with aspects of the present disclosure.

In addition to an MRI imaging system, certain examples discussed herein also utilize ultrasound data acquisition, such as to generate ultrasound images of the same general anatomic region scanned using an MRI system 10, but with a smaller field of view (i.e., MR images may typically be whole organ images, while ultrasound images instead tend to be parts of organs). With this in mind, and to provide familiarity with aspects of such an ultrasound imaging system, FIG. 2 illustrates a block diagram of an embodiment of an ultrasound imaging system 90 capable of acquiring ultrasound data of a patient undergoing imaging, including during an interventional procedure. In the illustrated embodiment, the ultrasound system 90 is a digital acquisition and beam former system, but in other embodiments, the ultrasound system 90 may be any suitable type of ultrasound system, not limited to the illustrated type. The ultrasound system 90 may include the ultrasound probe 94 and a workstation 96 (e.g., monitor, console, user interface, ultrasound signal processing circuitry) which may control operation of the ultrasound probe 94 and may process image data acquired by the ultrasound probe 94 and form images. The ultrasound probe 94 may be coupled to the workstation 96 by any suitable technique for communicating data and control signals between the ultrasound probe 94 and the workstation 96 such as a wireless, optical, coaxial, or other suitable connection.

The ultrasound probe 94 contacts the patient 26 during an ultrasound examination. The ultrasound probe 94 may include a patient facing or contacting surface that includes a transducer array 98 having a plurality of transducer elements 100 capable of operating in a switched manner between transmit and receive modes. Each individual transducer element 100 may be capable of converting electrical energy into mechanical energy for transmission and mechanical energy into electrical energy for receiving. It should be noted that the transducer array 98 may be configured as a two-way transducer capable of transmitting ultrasound waves into and receiving such energy from a subject or patient 26 during operation when the ultrasound probe 94 is placed in contact with the patient 26. More specifically, the transducer elements 100 may convert electrical energy from the ultrasound probe 94 into ultrasound waves (e.g., ultrasound energy, acoustic waves) and transmit the ultrasound waves into the patient 26. The ultrasound waves may be reflected back toward the transducer array 98, such as from tissue of the patient 26, and the transducer elements 100 may convert the ultrasound energy received from the patient 26 (reflected signals or echoes) into electrical signals for reception and processing by the ultrasound probe 94 and the workstation 96 to provide ultrasound images that may be analyzed. The number of transducer elements 100 in the transducer array 98 and the frequencies at which the transducer elements 100 operate may vary depending on the application.

As previously discussed, the ultrasound probe 94 is communicatively coupled to the workstation 96 of the ultrasound imaging system 90 to facilitate image formation and processing. As will be appreciated, the workstation 96 may include a number of components or features to control operation of the ultrasound probe 94, facilitate placement and/or guidance of the ultrasound probe 94, and facilitate production and/or interpretation of ultrasound data (including reconstructed ultrasound images). For instance, as illustrated, the workstation 96 may include a controller 104, processing circuitry 106, one or more user input devices 108, and a display 110. In certain embodiments, the workstation 96 may include additional elements not shown in FIG. 2, such as additional data acquisition and processing controls, additional image display panels, multiple user interfaces, and so forth.

The controller 104 may include a memory 112 and a processor 114. In some embodiments, the memory 112 may include one or more tangible, non-transitory, computer-readable media that store instructions executable by the processor 114 and/or data to be processed by the processor 114. For example, the memory 112 may include random access memory (RAM), read only memory (ROM), rewritable non-volatile memory such as flash memory, hard drives, optical discs, and/or the like. Additionally, the processor 114 may include one or more general purpose microprocessors, one or more application specific processors (ASICs), one or more field programmable logic arrays (FPGAs), or any combination thereof. The controller 104 may control transmission of the ultrasound waves into the patient 26 via the transducer array 98.

The processing circuitry 106 may include receiving and conversion circuitry. The processing circuitry 106 may receive the electrical signal data from the transducer array 98 of the ultrasound probe 94 representing reflected ultrasound energy returned from tissue interfaces within the patient 26. The processing circuitry 106 may process the data from the transducer array 98, such as correcting for noise artifacts, or the like. The processing circuitry 106 may then convert the signal data into an ultrasound image for presentation via the display 110. The controller 104 may cause display of the ultrasound image or images (or a construct or model generated based on such images or raw image data) produced by the processing circuitry 106 from the signal data received from the transducer array 98 of the ultrasound probe 94.

In operation, the controller 104 may receive a signal indicative of a target anatomy of the patient 26 and/or a target scan plane of the target anatomy via the one or more user input devices 108 of the workstation 96. The one or more user input devices 108 may include a keyboard, a touchscreen, a mouse, buttons, switches, or other devices suitable to allow the operator to input the target anatomy and/or the desired scan plane of the target anatomy. Based on the target anatomy and/or the target scan plane of the target anatomy, the controller 104 may output a signal to the transducer array 98 of the ultrasound probe 94 indicative of an instruction to convert the electrical energy from the ultrasound probe 94 into ultrasound waves and transmit the ultrasound waves into the patient 26 and to detect the ultrasound energy that is reflected back from the tissue interfaces within the patient 26.

Figure 3:
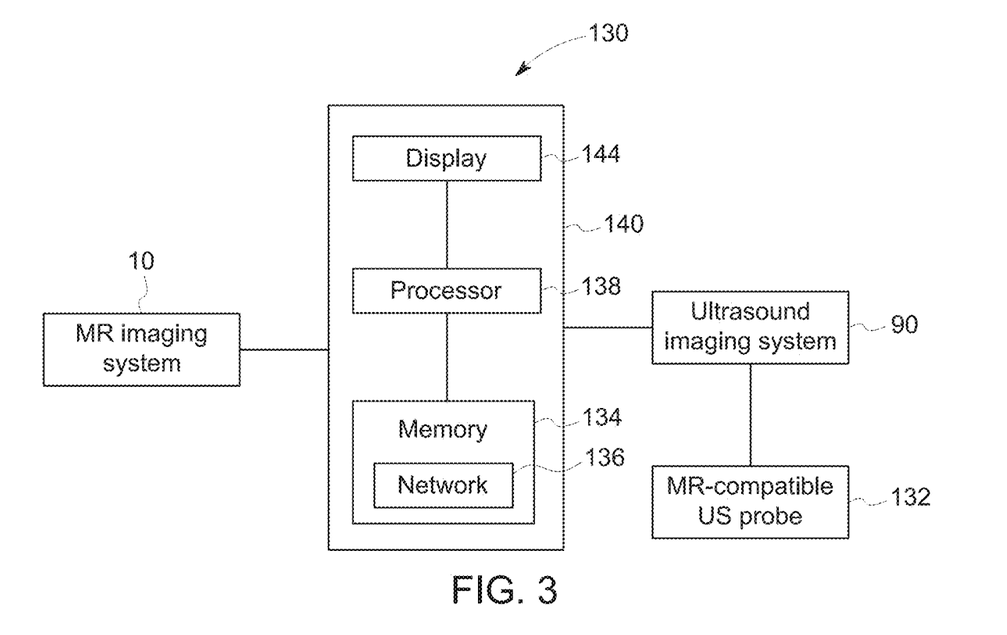
FIG. 3 illustrates a schematic diagram of an embodiment of a multi-modality imaging system, in accordance with aspects of the present disclosure.

With the preceding comments in mind, in certain embodiments, and as illustrated in FIG. 3, a combined MR and ultrasound imaging system 130 that may be used for non-invasive facilitation of surgical or interventional procedures may be provided. The combined MR and ultrasound imaging system 130 may be similar to the system described in U.S. patent application Ser. No. 15/870,519, entitled "Image-guided Biopsy Techniques", filed Jan. 12, 2018, which is incorporated by reference in its entirety for all purposes. The combined MR and ultrasound imaging system 130 includes some or all aspects of a magnetic resonance (MR) imaging system 10 and an ultrasound imaging system 90 as discussed herein.

The ultrasound imaging system 90 may be communicatively coupled to a MR-compatible ultrasound probe 132. The MR-compatible ultrasound probe 132 may be an ultrasound probe 94 configured for use in combination with the MR imaging system 10. As such, the MR-compatible ultrasound probe (as described in U.S. patent application Ser. No. 15/897,964, entitled "Magnetic Resonance Compatible Ultrasound Probe", filed Feb. 15, 2018, which is incorporated by reference in its entirety for all purposes) may contain low or no ferromagnetic material (e.g., iron, nickel, cobalt) content. The ultrasound probe 132, in one embodiment, is capable of three-dimensional (3D) volume acquisition with high temporal resolution, allowing an ultrasound image volume to be acquired at discrete time points. Moreover, besides being MR-compatible, the 3D ultrasound probe 132 in one such implementation is electronically steerable and hands-free. This allows the ultrasound image field-of-view to be electronically manipulated, obviating the need for robotic or mechanical ultrasound probe holders to change the imaging field-of-view. In this manner, simultaneous MR and ultrasound images can be easily acquired. Moreover, during the interventional procedure, the same ultrasound probe can be used and positioned in approximately the same manner as during the pre-interventional MR+ultrasound procedure without difficulty. This provides a further simplification of the workflow as approximately the same imaging set up is used between the pre-interventional and interventional procedure as the same ultrasound probe is utilized, and in the same manner.

In the depicted example, the combined MR and ultrasound imaging system 10 may further include a system controller 140 communicatively coupled to the other elements of the combined MR and ultrasound imaging system 130, including the MR imaging system 10 and the ultrasound imaging system 90. The controller 140 may include a memory 134 and a processor 138. In some embodiments, the memory 134 may include one or more tangible, non-transitory, computer-readable media that store instructions executable by the processor 138 and/or data to be processed by the processor 138. For example, the memory 134 may include random access memory (RAM), read only memory (ROM), rewritable non-volatile memory such as flash memory, hard drives, optical discs, and/or the like. Additionally, the processor 138 may include one or more general purpose microprocessors, one or more application specific processors (ASICs), one or more field programmable logic arrays (FPGAs), or any combination thereof. Further, the memory 134 may store instructions executable by the processor 138 to perform the methods described herein. Additionally, the memory 134 may store images obtained via the MR imaging system 10 and the ultrasound imaging system 90 and/or algorithms utilized by the processor 138 to help guide an interventional or surgical procedure based on image inputs from the MR imaging system 10 and the ultrasound imaging system 90, as discussed in greater detail below. The memory 134 may also store a neural network 138 that when trained functions to facilitate multi-modality image registration as described in greater detail below. In certain embodiments, the system 130 may be coupled to a remote database that includes the network 136. Further, the controller 140 may include a display 144 that may be used to display the images obtained by the MR imaging system 10 and the ultrasound imaging system 90.

It should be noted that the types of MR and ultrasound images acquired may vary. For efficiency and also to match acquisition frame rates, one embodiment has two-dimensional (2D) MR images acquired simultaneously with three-dimensional (3D) ultrasound images over time, i.e., matching time-series 2D MR images to time-series 3D ultrasound images at each time point. In this case, there is the possibility that endogenous fiducial structures/markers in the time-series 3D ultrasound images may not be common to the time-series 2D MR images. In certain embodiments, the MR images and/or ultrasound images may be stacked 2D images acquired over time.

Alternatively, sorting the time-series 2D MR images into corresponding collections, with each collection representing the same respiratory state, reformatted time-series 3D (4D) MR images that are temporally matched with the time-series 3D (4D) ultrasound images may be generated. This increases the probability that endogenous fiducial structures/markers in the ultrasound images are common in the MR images. However, even if this is not the case, the techniques disclosed below provide adequate matching or registration between MR and ultrasound images. In another embodiment, with sufficiently fast acquisition speeds, time-series 3D (4D) MR images are acquired simultaneously with time-series 3D (4D) ultrasound images to yield corresponding time-series 3D volume images that are temporally matched. As an MR image set at a reference time point and the corresponding ultrasound image volume are acquired at the same time point, the organ-of-interest visualized in MR and ultrasound have the same shape, orientation, and feature outlines, making the MR-to-ultrasound transformation an easier undertaking.

With the preceding in mind, and as discussed in greater detail herein, techniques are provided for combining MRI and real-time ultrasound imaging to provide physicians with the soft-tissue (e.g., brain tissue) image quality of MR images at the real-time frame rates of ultrasound. In one such example, multimodality image-guided neurosurgery, such as using the techniques discussed herein, aids surgeons in making clinical decisions to avoid damaging structures of the brain while resecting diseased tissue, such as tumor. In such a context, however, the brain may undergo significant non-linear structural deformation on account of dura opening and tumor resection. Intra-operative image guidance may be useful to a surgeon to facilitate complete resection of the tumor while avoiding other brain structures in the process. The techniques described herein addresses the issues of automatic registration of multi-modality images, particularly when such images have undergone deformable or affine transformations. Unlike image intensity and/or landmark-based deformable registration models, which may fail to deliver accurate real-time deformable registrations suitable for use in a neurosurgery procedure, the disclosed techniques provide a structure (e.g., brain structure) guided fast registration model. Registering of pre-operative MR images to intra-operative ultrasound in this manner allow continuous guidance, better visualization of the soft tissue and the tumor, and reduces surgery time and the complex and expensive logistics involved with intra-operative MRI.

Figure 4:
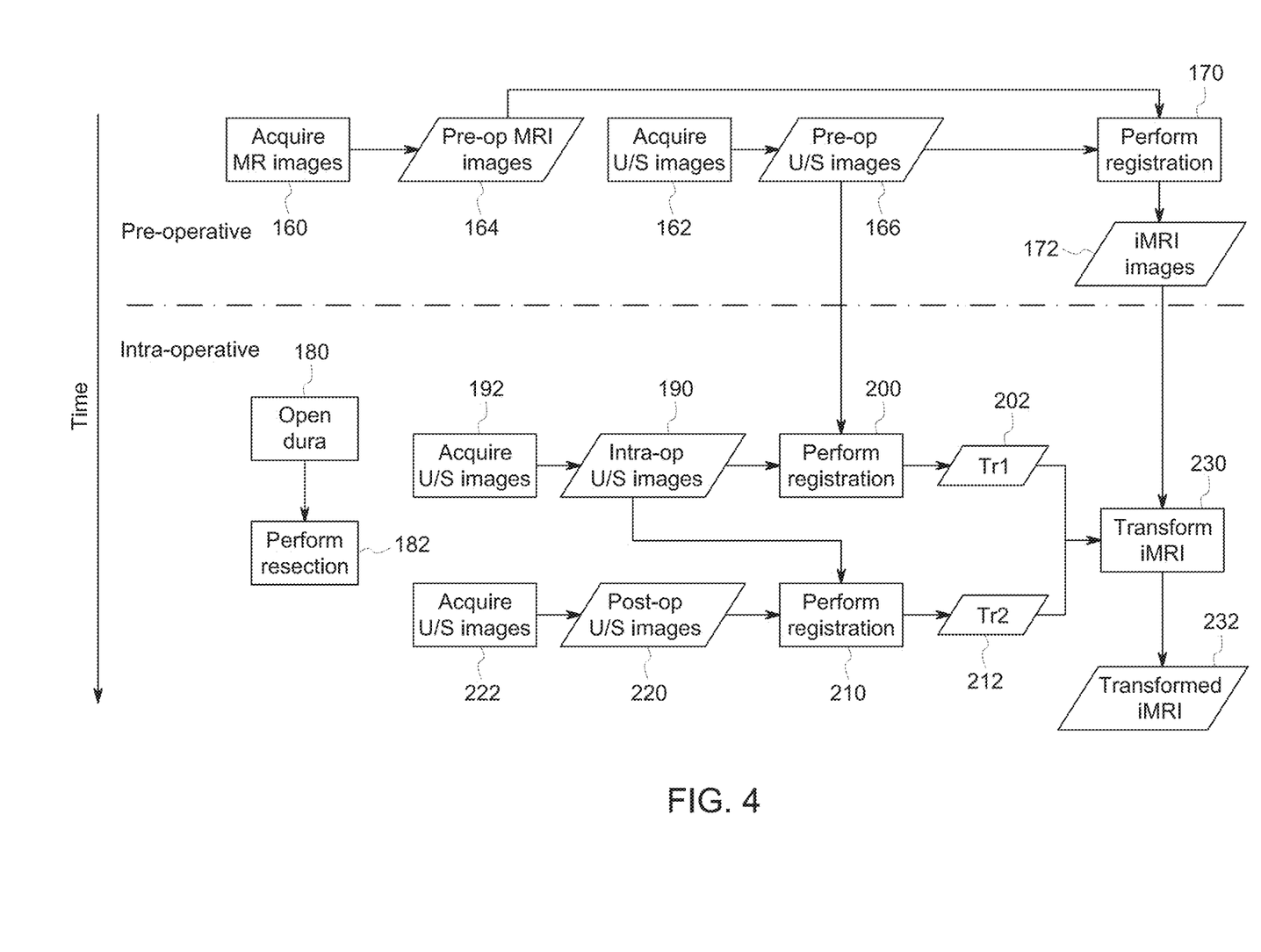
FIG. 4 illustrates an US-MRI fusion flowchart, in accordance with aspects of the present disclosure.

Turning to FIG. 4, a process flow of steps employed in accordance with one implementation is provided. In this example a pre-operation image acquisition (step 160 for MR images and step 162 for ultrasound images) is performed simultaneously (or near simultaneously, such as in temporally consecutive scans) to acquire pre-operative MR images 164 and ultrasound images 166. In one example, an MR-compatible 3D ultrasound probe 132 is used to allow the acquisition of the pre-operative ultrasound image data 166 concurrent with the acquisition of MR image data 164. Such simultaneous acquisition of multi-modality images improves pre-operative MRI and pre-operative ultrasound registration accuracy. This in turn enables a better initialization of a deformable registration between pre-operative MRI and intra-operative ultrasound, resulting in faster and more precise implementation. The MR images 164 that are registered (step 170) to pre-operative ultrasound images 166, as described herein, may be referred to as iMRI 172 herein to facilitate explanation of the registration processes.

Registration of the pre-operative MR images 164 and pre-operative ultrasound images 166 may be performed in different ways, depending on the acquisition context and other implementation-specific factors. For example, in a context where the pre-operative MR images 164 and pre-operative ultrasound images 166 are acquired separately, the images may be registered based on or using an electromagnetic tracker. However, in a simultaneous acquisition context, such as using a multi-modality system and MR-compatible probe 132 as shown in FIG. 3, an optical tracker or a fiducial visible in both the simultaneously acquired pre-operative MR images 164 and pre-operative ultrasound images 166 may be used to register the pre-operative images. Further, in some contexts where the initial registration is determined to be below a threshold quality, the pre-operative MR images 164 and pre-operative ultrasound images 166 may be re-registered at step 170 or the registration may be updated using structure-guided registration techniques as discussed herein.

In the depicted example, a surgical operation is then performed. In this example, a tumor resection is depicted in a brain surgery context, with the dura being initially opened (step 180) and a resection of a tumor performed (step 182). A deformable registration model based on brain structure (or other suitable anatomic structure) is applied (step 200) between pre-operative ultrasound images 166 (i.e., before dura opening) and intra-operative ultrasound images 190 (Acquired at step 192 after dura opening) to account for non-linear deformation of the brain tissue due to brain tissue shift associated with the opening of the dura at step 180. Such a nonlinear spatial transformation (Tr1) 202 provides a deformable registration (step 230) of the iMRI 172 to generate a transformed iMRI 232 as may be suitable for a neurosurgery procedure.

In the example context of brain surgery, after diseased tissue (e.g., a tumor) resection (step 182), a registration model based on brain structure (or other suitable anatomic structure) is applied (step 210) between intra-operative ultrasound images 190 (i.e., before resection) and post-operative ultrasound images 220 (acquired at step 222 after resection) to account for non-linear deformation of the brain tissue due to resection. This results in a second nonlinear transformation (Tr2) 212 that can be applied (step 230) to the iMRI 172 to generate or update a transformed iMRI 232 account for non-linear deformation of the brain tissue due to resection, which may be useful in evaluating the surgical outcome, such as to determine whether a surgical operation has been completed or additional resection is needed.

In one embodiment, applying the first transformation (Tr1) 202 to the iMRI 172 applies the effects of the dura opening to the iMRI 172 so that the transformed iMRI 232 corresponds to an MRI of the brain structures after opening of the dura. Applying both the first and second nonlinear transformations (i.e., Tr1*Tr2) to the iMRI 172 applies the effects of both the dura opening and the resection procedures to the iMRI 172 so that the transformed iMRI 232 corresponds to an MRI of the brain structures after opening of the dura and tissue resection, which may be useful in evaluating whether a surgical operation is complete. In this embodiment, the MRI 164 rigidly registered to the pre-operative ultrasound image 166 can be given the same nonlinear spatial transformation as the pre-operative ultrasound 166 could be given to bring the MRI 164 to intra-operative space. A multi-modality imaging system 130 as described in the preceding discussion using such a method can align the MRI 164 with real-time intra-operative ultrasound images 190 for surgical guidance, therefore providing surgeons with greater confidence about how much diseased tissue to resect to provide the best outcome for a patient.

By way of example, based on the transformed iMRI 232, guidance may be provided, such as by an image acquisition and/or analysis system as described herein, to a surgeon during or after an operation to facilitate the operation and/or to evaluate whether the operation has been successfully completed. For instance, such guidance may include displaying an image or sequence of images based on the transformed iMRI 232 which the surgeon may reference in performing the surgery or evaluating the surgery. In other contexts, guidance may be voice-based instructions that are audibly provided by the system and/or by virtual or augmented reality techniques which may, for example, display a tumor mesh on the ultrasound images displayed for the surgeon.

Figure 5A:
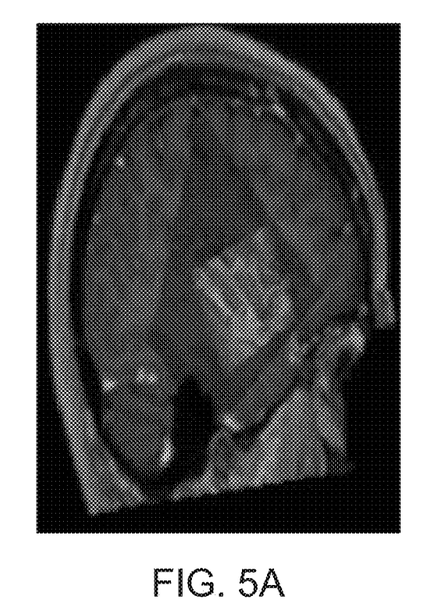
FIGS. 5A, 5B, 5C, and 5D illustrate image examples at different stages in an US-MRI fusion pipeline, in accordance with aspects of the present disclosure.

With the preceding in mind, FIGS. 5A, 5B, 5C, and 5D show MRI (FIG. 5A) and ultrasound images (FIGS. 5B-5D) demonstrating the effect of the structure guided deformable registration in a brain tumor resection surgery. In these examples, FIG. 5A shows an MRI 164 acquired pre-operation that is suitable for registration with a simultaneously or substantially simultaneously acquired ultrasound image 166. As noted herein the pre-operative ultrasound and MRI may be rigidly registered to generate an iMRI as discussed herein. As discussed herein, use of an MR-compatible 3D ultrasound probe built for simultaneous MR and ultrasound image acquisition improves pre-operative MRI and ultrasound registration accuracy.

Figure 5B:
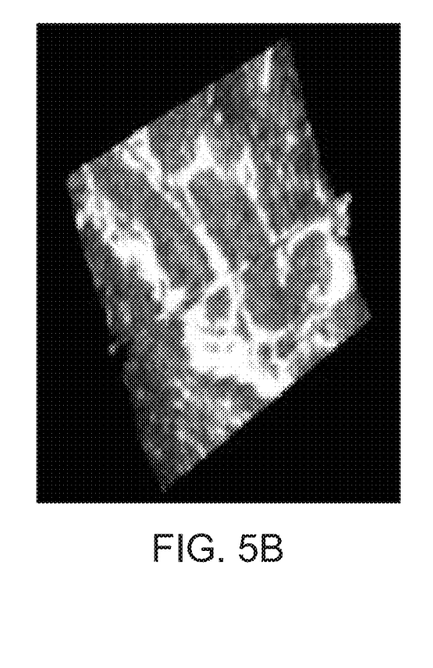
Figure 5C:
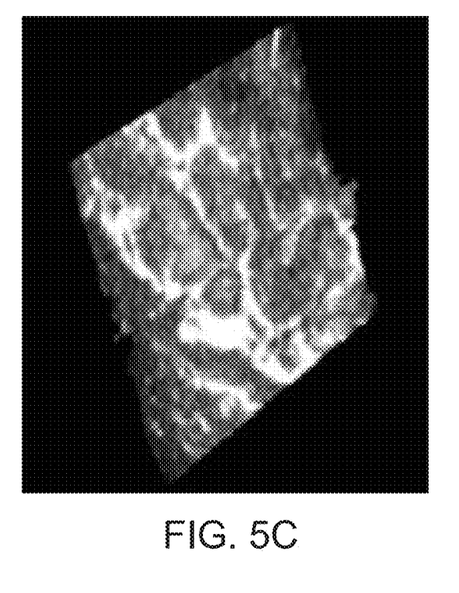
Figure 5D:
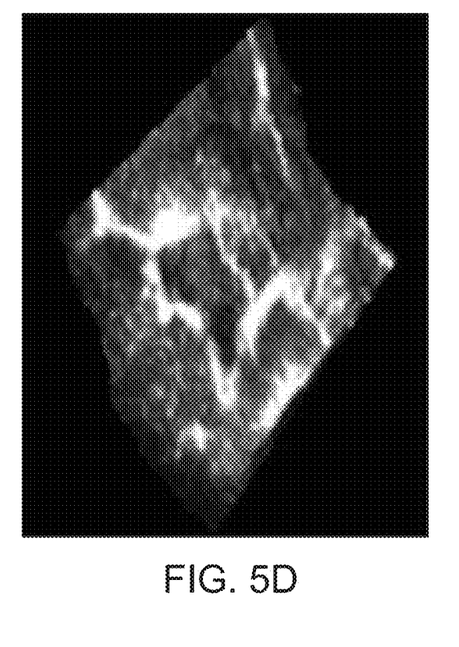

FIGS. 5B-5D illustrate ultrasound images acquired at different milestones within a procedure. Each of the ultrasound images, in one embodiment, are acquired using the same MR compatible probe as in pre-operative procedures. For example, FIG. 5B depicts an ultrasound acquired before opening of the dura in a brain surgery procedure. FIG. 5C depicts the same anatomic region after opening of the dura. FIG. 5D depicts the same anatomic region post-surgery, i.e., after resection.

Figure 6A:
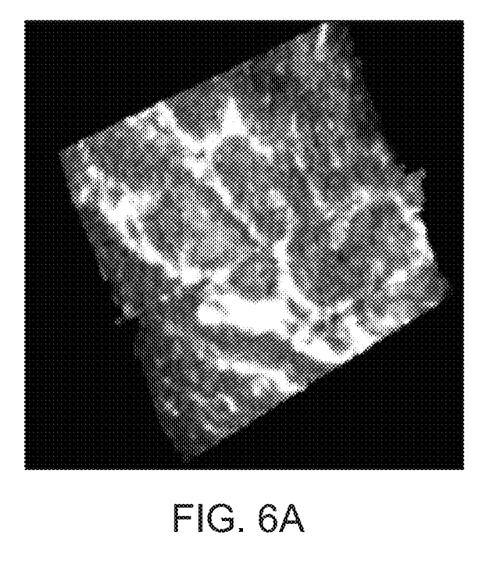
FIGS. 6A, 6B, 6C, 6D illustrate a set of clinical images showing pre-operative ultrasound to intra-operative ultrasound registration.
Figure 6B:
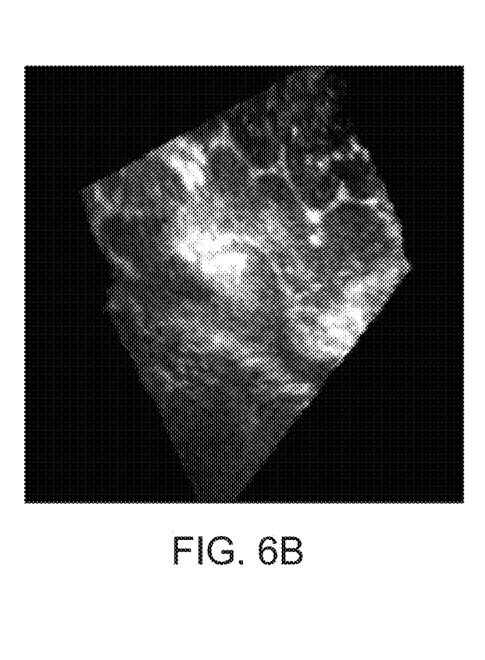
Figure 6C:
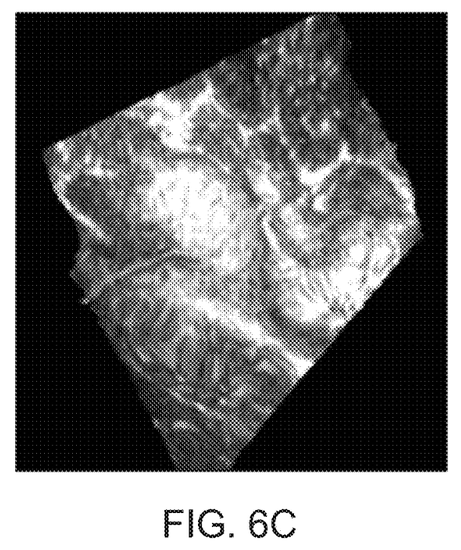
Figure 6D:
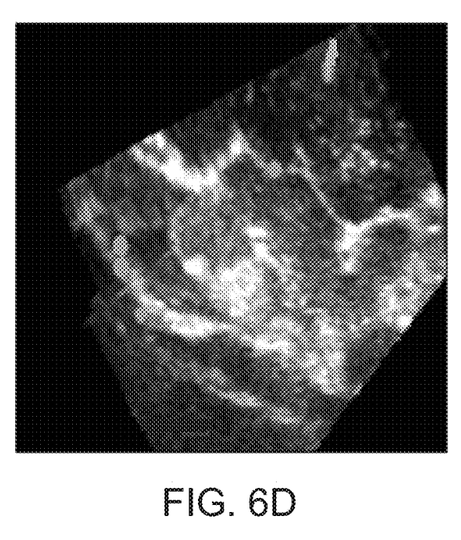

With the preceding in mind, FIGS. 6A, 6B, 6C, and 6D show a set of images illustrating the process of pre-operative ultrasound to intra-operative ultrasound registration as described herein. In the present example, the brain structures are automatically segmented within each image, such as using un-supervised or supervised machine learning or deep learning approaches (e.g., Gaussian mixture model, a neural network trained to segment and/or label different structures within an anatomic image), and followed by the deformation based on the segmented structures in pre-operative and intra-operative ultrasound images. With this in mind, FIG. 6A depicts a pre-surgery ultrasound image and FIG. 6B depicts an intra-surgery ultrasound image. Both images are input to an un-supervised or supervised machine learning or deep learning routine trained to segment anatomic structure, so that anatomic structure are segmented and labeled in both images. Turning to FIG. 6C, the correspondence between the segmented pre-operative and intra-operative brain structures of FIGS. 6A and 6B are identified and are utilized in a deformable registration (B-Spline, thin-plate spline, demons or optical flow) based on the segmented structures to generate a registered image. Deformable registrations parameters may be learnt a priori in a machine learning or deep learning framework. In this example, FIG. 6C shows a registered ultrasound image using segmented brain structure. The transform used to accomplish this registration may then be employed, as shown in FIG. 6D, to generate a transformed image corresponding to a real-time context that may be used to provide better guidance for surgeons in performing a surgery in real-time. Such structure guided registration that accounts for structural deformation due to brain shift and tumor resection is robust to image intensity variation and ultrasound imaging artifacts often observed in these images.

Figure 7:
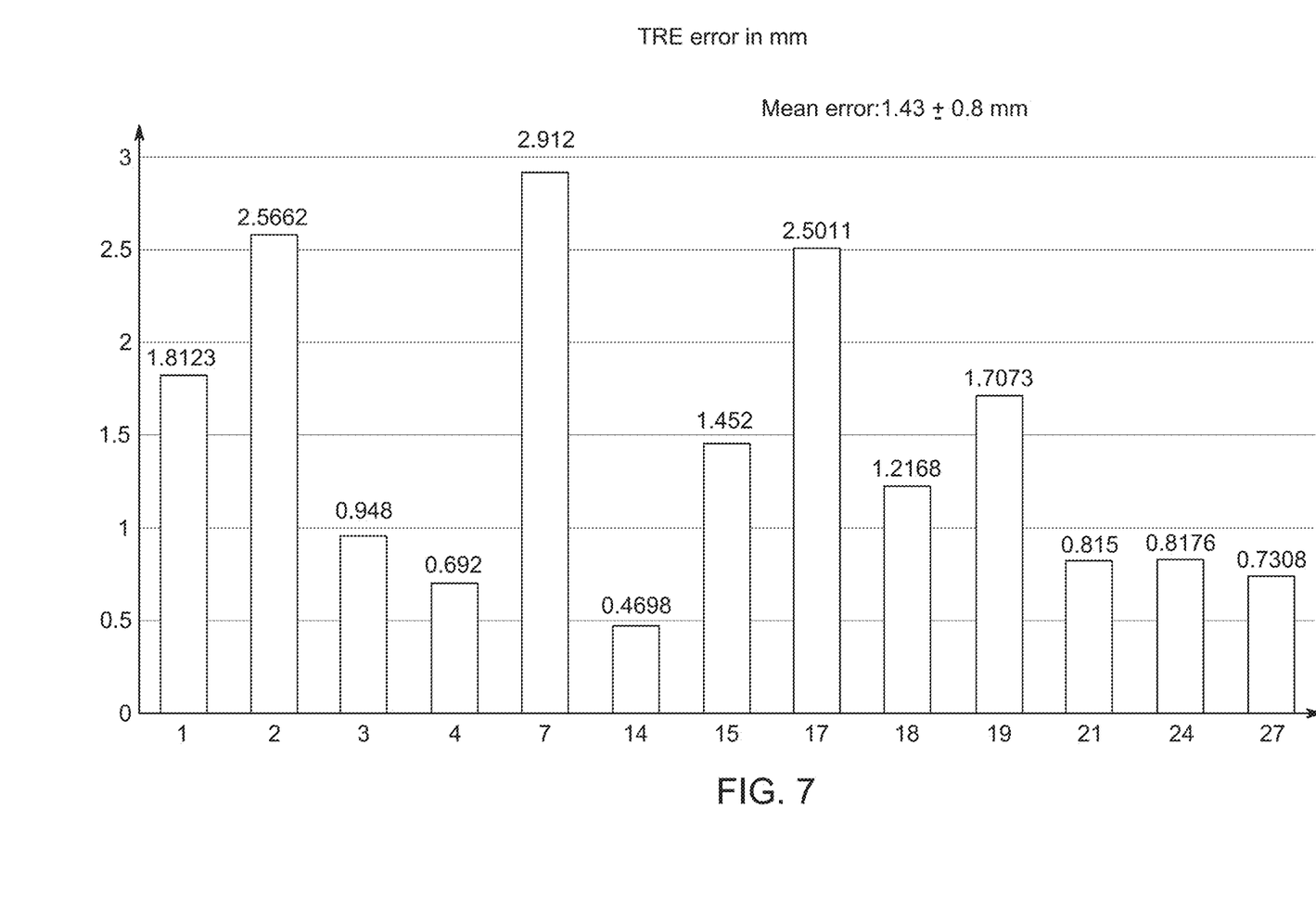
FIG. 7 presents the registration error from clinical validation testing.

The techniques described herein were validated using a public dataset having pre-operative ultrasound, intra-operative ultrasound, and pre-operative MRI. The registered images as illustrated in preceding examples were used for qualitative validation. In addition, the target registration error (TRE), presented in FIG. 7 can be used for quantitative validation. In this particular example, a mean target registration error of 1.4 mm (+/−standard deviation) was achieved. In clinical practice, mean error less than 2 mm is considered to be valid.

Technical effects of the disclosed embodiments include providing systems and methods related to automatic multi-modal image registration that utilizes anatomic structure-based segmentation, which may be accomplished using machine learning or deep learning based segmentation techniques, to facilitate accurate guidance in real-time tracking of moving, i.e., dynamic, anatomic objects. In particular, in one embodiment automatically segmented anatomic structures (e.g., brain structures) from pre-operative and intra-operative ultrasound images are used to drive a structure guided deformable registration to register pre-operative MRI to an intra-operative ultrasound domain. Such structure-guided registration is faster, more accurate, and robust to intensity variations and ultrasound imaging artifacts often encountered in routine medical procedure. Furthermore, in one embodiment an MR-compatible ultrasound probe is used for simultaneous acquisition of MRI and ultrasound in pre-operative stage. Such an acquisition improves the registration accuracy and allows better initialization for the subsequent deformable registrations. The pre-operative MRI, when adequately deformed using real-time ultrasound for guidance, may result in high tissue contrast visualization of the progress of the surgical resection procedure.

The technologies in this disclosure may be suitable to other problems related to automatic structure-guided rigid, affine or deformable registration. The structure to be registered can be automatically segmented using a machine learning or deep learning methods followed by a deformable registration model. Some potential additional implementations using the disclosed technologies may include 3D printing as required in additive manufacturing, and defect detection of parts in industrial application as a normalization step.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for image registration, comprising the steps of:
acquiring one or more pre-operative magnetic resonance (MR) images and one or more pre-operative ultrasound images;
performing a registration between the pre-operative MR images and the pre-operative ultrasound images;
acquiring one or more intra-operative ultrasound images during a surgical operation;
performing a structure-guided registration between the pre-operative ultrasound images and the intra-operative ultrasound images to derive a spatial transformation that accounts for non-linear deformations;
applying the spatial transformation to the pre-operative MR images that were registered to the pre-operative ultrasound images to generate one or more transformed MR images that align with the intra-operative ultrasound images; and
providing guidance based on the transformed MR images during the surgical operation to facilitate the surgical operation.

2. The method of claim 1, wherein the pre-operative magnetic resonance images are two-dimensional (2D) MR images and the pre-operative ultrasound images are three-dimensional (3D) ultrasound images.

3. The method of claim 1, wherein the pre-operative magnetic resonance images and the pre-operative ultrasound images are acquired simultaneously or in temporally consecutive scans.

4. The method of claim 3, wherein the pre-operative ultrasound images are acquired simultaneous with the pre-operative magnetic resonance images using a MR compatible ultrasound probe.

5. The method of claim 1, wherein the registration between the pre-operative MR images and the pre-operative ultrasound images is based on one or more of image intensity, landmarks, and/or structure.

6. The method of claim 1, wherein the intra-operative ultrasound images are acquired during the surgical operation using an MR compatible probe that was also used to acquire the pre-operative ultrasound images.

7. The method of claim 1, wherein the registration and the structure-guided registration are performed using automatically segmented brain structures that account for structural deformation due to brain shift and resection.

8. The method of claim 1, wherein the transformed MR images indicate the actual size, shape, position, boundaries, and/or orientation of an anatomy of interest during the surgical operation.

9. The method of claim 1, further comprising conducting a post-surgery procedure comprising the steps of:
acquiring one or more post-surgery ultrasound images;
performing an additional structure-guided registration between the intra-operative ultrasound images and the post-surgery ultrasound images to generate an additional spatial transformation;

applying the additional spatial transformation to the transformed MR images derived during the surgical operation to generate one or more post-operation transformed MR images; and providing guidance based on the post-operation transformed MR image regarding whether the surgical operation has been completed.

10. An image registration system comprising:
a memory encoding processor-executable routines; and
a processing component configured to access the memory and execute the processor-executable routines, wherein the routines, when executed by the processing component, cause the processing component to perform actions comprising:
  accessing or acquiring one or more pre-operative magnetic resonance (MR) images and one or more pre-operative ultrasound images;
  registering the pre-operative MR images and the pre-operative ultrasound images;
  receiving one or more intra-operative ultrasound images generated during a surgical operation;
  performing a structure-guided registration between the pre-operative ultrasound images and the intra-operative ultrasound images to derive a spatial transformation that accounts for non-linear deformations;
  applying the spatial transformation to the pre-operative MR images that were registered to pre-operative ultrasound images to generate one or more transformed MR image that align with the intra-operative ultrasound images; and
  providing guidance based on the transformed MR images during the surgical operation to facilitate the surgical operation.

11. The image registration system of claim 10, wherein the pre-operative magnetic resonance images and the pre-operative ultrasound images are acquired simultaneously or in temporally consecutive scans using a MR compatible ultrasound probe.

12. The image registration system of claim 10, wherein the registration between the pre-operative MR images and the pre-operative ultrasound images is based on one or more of image intensity, landmarks, and/or structure.

13. The image registration system of claim 10, wherein the registration and the structure-guided registration are performed using automatically segmented anatomic structures that account for structural deformation of the anatomy during the surgical operation.

14. The image registration system of claim 10, wherein the transformed MR images indicate the actual size, shape, position, boundaries, and/or orientation of an anatomy of interest during the surgical operation.

15. The image registration system of claim 10, wherein the routines, when executed by the processing component, cause the processing component to perform further actions comprising:

accessing or acquiring one or more post-surgery ultrasound images;

performing an additional structure-guided registration between the intra-operative ultrasound images and the post-surgery ultrasound images to generate an additional spatial transformation;

applying the additional spatial transformation to the transformed MR images derived during the surgical operation to generate one or more post-operation transformed MR images; and providing guidance based on the post-operation transformed MR image regarding whether the surgical operation has been completed.

16. A method for evaluating a surgical operation, comprising:
  acquiring one or more pre-operative magnetic resonance (MR) images and one or more pre-operative ultrasound images;
  performing a registration between the pre-operative MR images and the pre-operative ultrasound images;
  acquiring one or more post-surgery ultrasound images;
  performing a structure-guided registration between the post-surgery ultrasound images and one of either the pre-operative ultrasound images or an intermediate transform of the pre-operative ultrasound images to derive a spatial transformation that accounts for non-linear deformations;
  applying the spatial transformation to the pre-operative MR images or an intermediate transform of the MR images to generate one or more post-operation transformed MR images; and
  providing guidance based on the post-operation transformed MR image regarding whether the surgical operation has been completed.

17. The method of claim 16, wherein the intermediate transform of the pre-operative ultrasound images is generated using an additional spatial transformation generated by performing an additional structure-guided registration between the pre-operative ultrasound images and one or more intra-operative ultrasound images.

18. The method of claim 16, wherein the registration and the structure-guided registration are performed using automatically segmented anatomic structures that account for structural deformation of the anatomy due to the surgical operation.

19. The method of claim 18, wherein the anatomy is a brain and the anatomic structures are brain structures.

20. The method of claim 16, wherein the transformed MR images indicate the actual size, shape, position, boundaries, and/or orientation of an anatomy of interest after the surgical operation.

* * * * *